United States Patent [19]
Barron

[11] 3,984,666
[45] Oct. 5, 1976

[54] CALORIE METERING EXERCISER

[76] Inventor: Benjamin Barron, 1335 143rd St., Whitestone, N.Y. 11357

[22] Filed: May 23, 1974

[21] Appl. No.: 472,812

[52] U.S. Cl. ............................. 235/151.3; 73/379; 235/92 MT; 235/92 NT; 272/73; 322/28
[51] Int. Cl.² ..................... G01L 5/02; H02P 9/30
[58] Field of Search .......... 235/151.3, 92 T, 92 CA, 235/92 NT, 92 MT; 73/379, 190 R, 193 R; 128/2.05 R, 2.06 R; 272/DIG. 6, 73; 322/28, 69, 70

[56] References Cited
UNITED STATES PATENTS

| | | |
|---|---|---|
| 3,192,772 | 7/1965 | Tarter ................................. 73/379 |
| 3,505,992 | 4/1970 | Jaeger ............................ 272/DIG. 6 |
| 3,511,097 | 5/1970 | Corwin ................................ 73/379 |
| 3,568,041 | 3/1971 | Arakane .............................. 322/28 |
| 3,705,721 | 12/1972 | Lulay et al. ..................... 272/DIG. 6 |
| 3,820,009 | 6/1974 | Itoh et al. ............................ 322/28 |
| 3,858,108 | 12/1974 | Bray.................................... 322/28 |
| 3,869,121 | 3/1975 | Flavell ........................... 272/DIG. 6 |

*Primary Examiner*—Malcolm A. Morrison
*Assistant Examiner*—Errol A. Krass

[57] ABSTRACT

An exerciser combined with means for converting the output energy to measurable form and adjusting the indicated energy output by the exerciser to a quantity of exercise desired and means for measuring the energy output of the exerciser in calories.

11 Claims, 7 Drawing Figures

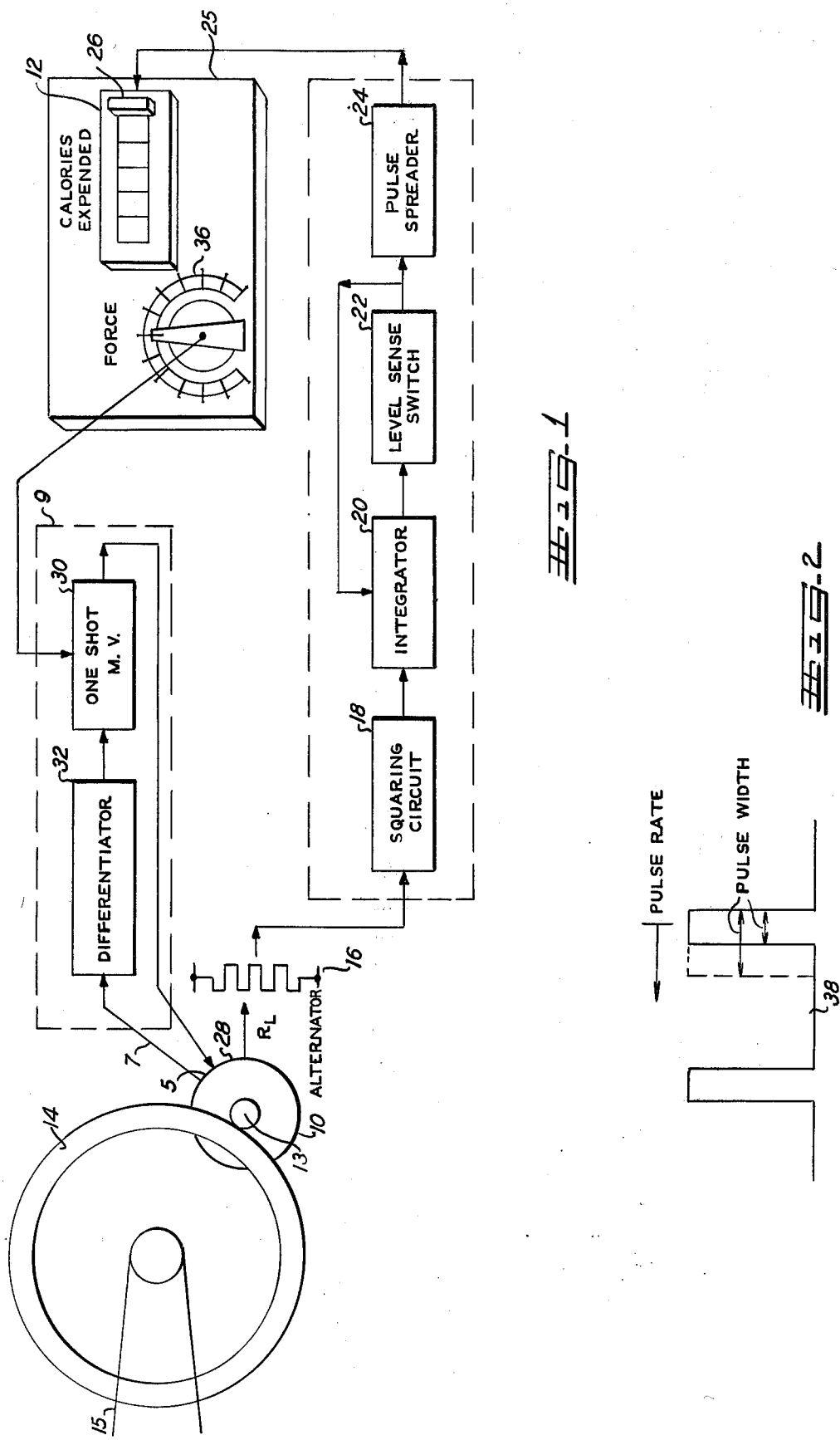

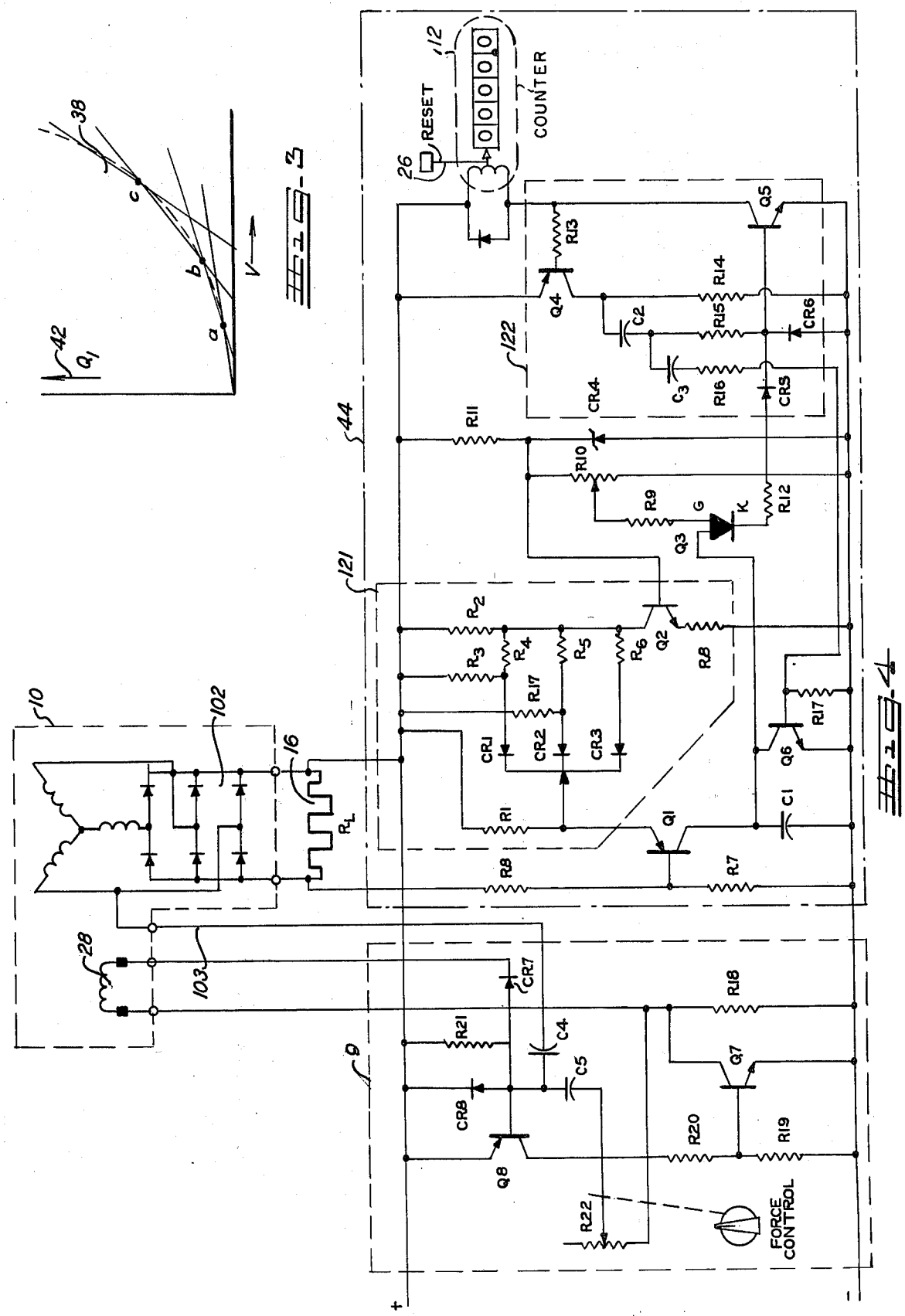

CALORIE METERING EXERCISER

This invention relates to an energy absorbing exerciser, and more particularly to an exercise system in which the working force felt by the exerciser can be adjusted by the exerciser, continuously and smoothly, and the total energy expended by the exerciser is measured quantitatively, continuously and the quantity is visibly displayed.

The ratio of calories burned and oxygen expended is fixed, whereby this simple measure of calories expended is useful as a measure of oxygen consumed. Therefore, the display of calories consumed is a true indication of the amount of aerobic exercise accomplished by the exerciser.

It is also desirable to control the reaction force felt by the exerciser during this work-out. That is, he may condition himself as he proceeds, starting off at low force levels and working his way upward towards heavier loading. It is desirable that the force adjustment be easily made while exercising and without interruption. The calories consumed measurement should be independent of the force level adjustment, thereby maintaining the measurement of the exercise in terms of the calories expended accurate and visible.

These are desirably accomplished using an exercise machine which displays the force quantity, such as in calories expended clearly and accurately; and control of the force level felt, be supplied smoothly and precisely, without sudden fluctuations due to system instabilities or sudden speed changes by the exerciser.

The display and control dials are calibrated so that an exerciser can easily judge for himself how he is proceeding with his exercise program or his physician can readily prescribe what caloric expenditure and force levels he may safely use.

It is the object of my invention to provide an exercise machine using a single modified automotive type alternator coupled to novel electronic control circuitry.

The drawings herewith illustrate practical combinations of apparatus elements useful to practice this invention.

In the drawings,

FIG. 1 is a block diagram of the invention;
FIG. 2 is a pulse diagram;
FIG. 3 is a control curve;
FIG. 4 is a general wiring diagram.

A stationary bicycle, treadmill or rowing machine are typical machines that can be used as exercise devices for this purpose, a portion being shown coupled to output measurement means only diagrammatically, and any of the common structures may be substituted.

Referring to the block diagram, FIG. 1, the essential parts of the calorie measuring force setting exerciser comprise an alternator-rectifier 10 is shown driven by a wheel 14 frictionally, such as a bicycle wheel bearing against a drive pulley fastened to its armature shaft 13. The wheel 14 may be driven through a drive belt 15, pedaled by force supplied by the exerciser. Thus, the total energy input to the alternator comes from the exerciser.

The output power of the alternator-rectifier is absorbed by a loading resistor 16. Thus, as the individual exerises such for example, as by pedaling a bicycle-like device, his physical work output is converted to electric power by the alternator-rectifier 10 to be dissipated as heat by the load resistor 16.

The value of the load resistor 16, is known from the familiar expression, $p = V^2/R$ i.e., the square of the voltage $V$ across the load $R$ of resistor 16, is a measure of the power $P$ being produced by the alternator-rectifier, and thus, is a measure of the rate of energy being expended by the exerciser. This voltage $V$ is sensed by a squaring circuit 18. This circuit has its output current directly proportional to the square of the signal voltage ($V^2$) input. The current flowing out of the squaring circuit 18 is thus proportional to the power $P$ of the exerciser in electrical terms dissipated in the load resistor 16, and that current is thus proportional to the rate of energy being expended by the exerciser.

The current output from the squaring circuit 18 is fed to an integrator 20. The volage produced by the integrator is proportional to the integral of the current supplied thereto with respect to time. The integrator output voltage Vo is then proportional to the integral of the square of the voltage $V$ input to the squaring circuit 18 and is thus proportional to the total energy expended by the exerciser in a given interval of time. Expressed mathematically:

Integrator output voltage, $$Vo = \int_o^T i\, dt$$

The squaring circuit 18 output current, $i = K_1 V^2$
Therefore, $$Vo = \int_o^T K_1 V^2 dt$$

where $k_1$ is a constant of proportionality.
Now, $V^2 = K_2 P$ where $P$ the power output or rate of energy expended by the exerciser and $K_2$ is a second constant of proportionality.
Then $$\frac{Vo}{K_1 K_2} = \int_o^T P\, dt = \Delta W$$

where $\Delta W$ equals the increment of energy expended by the execiser in the time interval T.

The integrator 20 output voltage feeds a level sensing switch 22 which will trip, interrupting the circuit, when a voltage in excess of a preset level is fed into it. When the level sense switch 22 trips, it resets the integrator to zero where is repeats the cycle, that is, allows it to start integrating again. The switching voltage level of 22 is adjustable to allow tripping at any desired quantity of expended energy, $\Delta W$.

The level sense switch 22 output signal feeds a pulse spreader 24 which in turn drives a resetable mechanical counter 26 stepwise. The level sense switch 22 can be set to trip at any input voltage, and correspondingly by any discrete quantity of energy $\Delta W$. Thus, the trip level is adjusted to a recognizable quantity of expended energy for example, 0.1 kilocalories. One kilocalorie of expended physical energy is commonly called one "calorie" by nutritionists. The counter then is made to step once for a selected discrete recognizable quantity of expended energy by the exerciser for example, 0.1 kilocalorie.

Since the trip point, Vo, is directly proportion to ΔW, the counter thus displays the total energy expended by the exerciser, totalizing such recorded increments of energy expended, andsinge ΔW, can be chosen to be a recognizable unit of energy, for example, the 0.1 nutritional calories expended, the counter then is made to display the total energy expended by the exerciser during the period he is exercising. The increment of energy, ΔW, can be calibrated to the quantity of energy expended, as stated, but it can also be calibrated with a correction factor, to relate the reading of the counter 26 to display nutritional calories burned by the exerciser.

The publication "Rehabilitation and Medicine" by S. Light 1968 by Waverly Press, page 656, lists rates of nutritional calories expended for various forms of exercise. Considering that the energy expended charts are based upon measurements for a standard 150 pound person, it follows that the thermodynamic efficiency of a human is 0.16. That is, to deliver one nutritional calorie of energy output, the exercise must give up 6.25 stored nutritional calories. Consequently, the counter can be calibrated to continuously display to the exerciser the total nutritional calories he has given up, or "burned" from the start of his exercise period to the instant he observes the reading on the counter 26. In this manner the exerciser can observe the amount of aerobic exercise he has done accurately and independent of the speed at which he has worked.

It is also recognized by the inventor that all exercisers differ. Various exercising devices that may be used herewith, differ and the optimum rate of work, or how "hard" one can work, may differ greatly between individuals. Further, it is desirable to allow the exerciser himself to conveniently adjust the level of work rate he is doing at various times during his exercise period as his body conditioning changes. This is accomplished by controlling the field 28 of the alternator 10.

A novel means for alternator field control may be used which allows adjustment of the opposing force by the alternator, as felt by the exerciser. The force felt by the exerciser is smoothed by preventing force pulsations through this novel control system.

Power=Force × Velocity. Therefore it follows, that Force=Power divided by Velocity. Further, automotive type alternators are designed specifically for battey charging. They have a high synchronous impedance. The synchronous impedance, $X_d$, is given by the expression, $X_d=2\pi f L_d$ where $f=$ the electrical frequency of the alternator, $L_d=$the synchronous inductance.

$X_d$ is large, so that the output current of the alternator is nearly independent of loading resistance. Therefore, the output current of the alternator can be expressed by:

$$I_g = \frac{E_{gen}}{X_d} = \frac{E_{gen}}{2\pi f L_d}$$

where Egen is the open circuit generated voltage of the alternator and $E_{gen}=K_1 \times f \times I_f$ where $K_1$ is a constant, $f$ is the generator frequency and is directly proportional to the exerciser speed, S, and $I_f$ is the field current. Then, $$I_g = \frac{K_1 f I_f}{2\pi f L_d} = \frac{K_1}{2\pi L_d} I_f$$

This expression shows that the generator output current is independent of the generator frequency.

Since $2\pi L_d$ is constant, it follows that $I_q=K_3 I_f$ (where $K_3$ is a constant) tends to be fixed, independent of shaft speed. This, of course, is ideal for battery charging in an automobile, but must be corrected for this invention for the following reasons:

Output power from the alternator is $P_o=(I_q)^2 R_L=(K_3)^2 I_f^2 R L$.

Since $R_L$ is constant, $P_o=K_4 I_f^2$ where $k_4$ is a constant.

Now, $P_o=F \times S$ where $F=$the force felt by the exerciser.

Then, $F \times S = K_4 I_f^2$ or $F=K_4 I_f^2/S$

Thus, if the field current were held constant, the force felt by the exerciser would decrease when the speed at which he is exercising increases. At low speeds, he would be working against a high opposing force, which would ease off as he speeds up. Because of the negative force vs speed characteristic and the time delay in human response to stimuli, the exerciser could not maintain a predetermined rate of speed. Instead he would move in a jerky, start-stop unstable manner.

This characteristic is eliminated through the means of alternator field control used in this invention. The generator field current is made to be directly proportional to alternator frequency, $f$, and is thus directly proportional to exerciser speed, S. Then where $K_5$ is a constant of proportonality.

$$\text{Then, } F = K_4 \frac{(K_5)^2 S^2}{S} = K_4 S (K_5)^2$$

It now follows that the force felt by the exerciser increases with speed. He feels low opposing force at low speeds which then increase as he speeds up, allowing his to work smoothly. Further, $K_5$ is made adjustable, allowing him to adjust the opposing force level he feels at any speed. Thus, he may set the force level corresponding to his optimum work-out speed by matching his rate of nutritional calorie expenditure to his physical capabilities. The exerciser now can continuously adjust his work load to allow for "warm up" during the exercise period to maximize his nutritional calories expenditure while preventing premature exhaustion.

Refering to FIG. 1, the generator output frequency signal, which is a square wave, is fed to a one-shot multivibrator 30, through a differentiator 32. The duration of the "on" time of the multivibrator 30 is controlled by a rheostate 36 which is located within easy reach of the exerciser. The multivibrator 30 produces a train of voltage pulses 38 as shown in FIG. 2, at a rate equal to the alternator frequency, and thus a rate proportional to the exerciser's speed. The alternator field 28 is highly inductive. The d.c. field current, $I_f$, is then directly proportional to the exerciser's speed due to the smoothing action of the alternator field inductance. Further, since the pulse width is controlled, as shown in FIG. 2, the average alternator field current at a particular speed is also set by the exerciser.

At any exercise speed, the force felt by the exerciser at that speed is continuously and smoothly adjustable at 36 thereby achieving the desired adjustable, smooth exercising rate. The counter 26 displays total energy used, independently of the rate of force expenditure. Thus, the exerciser observes the correct quantity of calories he has expended independently of how fast or how hard he is working.

Detailed circuitry of the electric system devised to accomplish the foregoing are illustrated in FIG. 4.

Alternating current produced by the alternator 10 is converted to d.c. by a rectifier bridge 102. The resulting current is fed to a load resistor 16 which dissipates the power produced by the alternator 10. The voltage across the load resistor 16 is fed to a transistor Q1, through resistor R8, as shown in FIG. 4. A "squaring" network 121 forms the emitter current of Q1. Since there is a finite forward drop across the diodes in the rectifier bridge 102, the squaring network 121 is arranged to follow a corrected square law curve:

$$P_0 = \left(\frac{V^2}{RL}\right) + 2V_d \frac{V}{RL}$$

Where $V$=the voltage developed across the load resistor $R_1$, and
$V_d$=diode forward drop voltage.

The resistor-diode network 102 is arranged to fit the corrected square law curve 38 (FIG. 3). The exact curve 40 of Q1 collector current, $i_q$, 42, is shown dotted. As the voltage across $R_2$ increases from zero, current $i_q$ follows a straight line curve 0 to $a$ and is proportional to $R_1$. When the current reaches point $a$, the voltage developed across $R_1$ exceeds the bias voltage across R3. Current $i_q$, now follows the straight line $a$ to $b$ and is now proportional to R1, parallel to the equivalent resistance value of R3, R4 and R2.

In a similar manner, the curve is fitted at points $b$ and $c$. Points $a$, $b$, $c$, etc. are selected to have the best fit to the desired square law curve and are not necessarily limited to three points. The collector current $i_q$, is thus proportional to the rate of energy expenditure of the exerciser.

Capacitor C1, integrates current $i_q$. Thus, the voltage is proportional to an increment of energy expended by the exerciser. Transistor Q3 is a programmable unijunction transistor (P.U.T). Its trip level is set by a calibration potentiometer, R10. When the voltage across C1 exceeds this preset level, Q3 fires and produces a voltage pulse to Q5 through CR5. As described before, the trip level for Q3 is set to correspond to a recognizable quantity of expended nutritional calories. The pulse to Q5 triggers a power pulse stretcher circuit 122. The duration of the pulse is long enough to assure the counter 26 advances one step.

Another output voltage from the pulse stretcher 122, is fed throug a differentiating circuit C3 and R16 to turn on the reset transistor Q6. Q6 discharges the integrating capacitor C1, completely. This resets the energy measuring system 44, to commence integrating the oncoming energy signal from load resistor 16, to repeat the squaring and integrating cycle.

The calorie counter 12 is fitted with a reset 26, so that the calorie count can be made to start from zero at the commmencement of the exercise period.

The alternator field control system 9 receives its alternator frequency signal directly from an alternator a.c. winding 103. This signal is essentially a square wave due to the reaction between the high synchronous impedance of the alternator, the essentially d.c. voltage across the load resistor 16, and the clamping action of the bridge rectifier diodes 102.

The square wave is differentiated by C4 to produce short pulses to turn on Q8. Q8 turns on Q7. The collector voltage of Q7 is fed back, positively, to Q8 through R22 and C5 to keep Q8 on, and thus keep Q7 on. The time duration of this on period is determined by the time constant of R22 and C5. If R22 is decreased, the pulse duration from Q7 decreases.

Output current from Q7 drives the alternator field 28. Since the field is highly inductive, the average value of the field current is thus proportional to pulse frequency and the pulse duration set by R22. R22 is located on the display panel 25, to be conveniently available for adjustment by the exerciser.

This invention achieves the desired effects of providing an exerciser a smooth, easily adjustable force load and an easily observed measure of his calorie expenditure that totalizes his calorie usage independent of how fast or hard he is exercising.

I claim:

1. An exercising device including elements movable by the user to rotate an alternator means connected to absorb energy expended in operation of said device, means reacting proportional to the rotational speed of said alternator for controlling the force expended by the user, means for detecting the output of the alternator corresponding to the rate of expenditure of energy transferred to said alternator by said user, said detecting means producing an output; means for converting said output of the detecting means into electric pulses, each of said pulses having a magnitude proportional to a predetermined increment of said absorbed energy and an impulse advanced counter means for counting and visibly displaying the number of electric pulses produced by said converting means.

2. Exercising device as defined in claim 1, further comprising means for converting the alternating current output of said alternator to unidirectional current, and fixed resistor means for absorbing said unidirectional current.

3. Exercising device as defined in claim 2, wherein said means for detecting the rate of expenditure of energy comprises a squaring circuit, said squaring circuit means producing a current proportional to the square of the value of said voltage across said resistor.

4. Exercising device as defined in claim 3, further including a capacitor means for accumulating said current for producing a voltage whose value is proportional to the integral of said current, a voltage level sensing switch for generating a pulse signal when said capacitor voltage reaches a selected amplitude, means for resetting said capacitor voltage to zero by said pulse, means for coupling said pulse to said impulse advanced counter and means for resetting said counter to zero.

5. Exercising device as defined in claim 2, wherein the said alternator includes direct current controlled field winding means for controlling the output current of said alternator.

6. Exercising device as defined in claim 5, wherein said direct current control means for alternator output current includes means for sensing the frequency of said alternator, said frequency sensing means triggering a one-shot multivibrator at a rate equal to the alternator frequency, rheostat means for setting the width of each of the pulses produced by said multivibrator, and means for coupling said pulses to the alternator field winding introducing unidirectional current into the said field winding having a magnitude proportional to the product of said alternator frequency and said pulse width.

7. Exercising device as defined in claim 3, including potentiometer means for adjusting said voltage level sensing switch to trip at a voltage level equivalent to a predetermined quantity of energy expended by said exerciser, said quantity of energy being calibrated in terms of nutritional calories expended by said exerciser.

8. In combination, an alternator having a field winding and an alternating current output producing a voltage proportional to the rotational speed of said alternator, means for applying a rotational force to rotate said alternator a one shot multivibrator connected to one phase of said alternator tripping in synchronism with each alternation thereof, a rheostat in said multivibrator circuit manually adjustable to set the width of each pulse of said multivibrator, and means coupling said pulses to the alternator field winding producing direct current in said field winding having a magnitude proportional to the product of said alternator frequency and said pulse width.

9. Apparatus for indicating energy expended and work done by an individual, comprising electrical alternator means to be mechanically driven by said individual for providing an alternator output voltage, means for modifying the output voltage of said alternator to a value proportional to the energy and work done by said individual, means for receiving said alternator output voltage and providing a series of pulses having a repetition rate proportional to the square of the amplitude of said alternator output voltage, and counter means for receiving said series of pulses and providing an indication of the number of pulses received.

10. Apparatus for indicating and controlling energy expended and work done by an exercising individual comprising electrical alternator means to be mechanically driven by said individual for providing an alternator output voltage, a force controller increasing the field of said alternator in direct proportion to its rotational speed applied by said individual, means for receiving said alternator output voltage and providing a series of pulses having a repetition rate proportional to the square of the amplitude of said alternator output voltage, and counter means for receiving the series of pulses and providing an indication of the number of pulses received.

11. Apparatus as defined in claim 8, wherein said one shot multivibrator includes a rheostat manually adjustable to set the width of each pulse of said multivibrator.

* * * * *